United States Patent [19]

Oehler et al.

[11] Patent Number: 4,740,086

[45] Date of Patent: Apr. 26, 1988

[54] APPARATUS FOR THE PHOTOACOUSTIC DETECTION OF GASES

[76] Inventors: Oskar Oehler, Streulistrasse 24, 8032 Zürich; Klaus Mosbach, Rebbergstrasse 83, 8102 Oberengstrigen; Martin Seifert, Elionorenstrasse 16, 8032 Zürich; Heinrich Kunz, Preyerstrasse 16, 8001 Zurich; Niels Kuster, Bodmerstrasse 6, 8002 Zurich, all of Switzerland

[21] Appl. No.: 796,616

[22] PCT Filed: Jan. 30, 1985

[86] PCT No.: PCT/CH85/00014

§ 371 Date: Oct. 7, 1985

§ 102(e) Date: Oct. 7, 1985

[87] PCT Pub. No.: WO85/03574

PCT Pub. Date: Aug. 15, 1985

[30] Foreign Application Priority Data

Feb. 7, 1984 [CH] Switzerland .............................. 572/84
May 28, 1984 [CH] Switzerland ............................ 2594/84
Sep. 6, 1984 [CH] Switzerland ............................ 4249/84

[51] Int. Cl.[4] ........................................... G01N 21/00
[52] U.S. Cl. ..................................... 356/432; 356/51; 250/343
[58] Field of Search ................. 356/51, 432; 250/343, 250/353, 356.1; 55/158; 73/24

[56] References Cited

U.S. PATENT DOCUMENTS 4,051,372 9/1977 Aine .
4,188,543 2/1980 Brunsting et al. .............. 356/318 X
4,197,369 4/1980 Weaver .
4,220,715 9/1980 Ahnell .
4,557,603 12/1985 Oehler et al. .................... 250/343 X

FOREIGN PATENT DOCUMENTS 2643414 9/1976 Fed. Rep. of Germany .
55-47437 6/1980 Japan .
55-47436 6/1980 Japan .
8202950 9/1982 PCT Int'l Appl. .

OTHER PUBLICATIONS

Rosengren, Optimal Optoacoustic Detector Design, Applied Optics, vol. 14, No. 8, Aug. 1975, pp. 1960-1976.
Bults et al., Photoacoustic Measurements of Photosynthetic Activities in Whole Leaves Photochemistry and Gas Exchange, Biochimica et Biophysica Acta (1982), pp. 452-465.
Cahen, Photoacoustic Cell for Reflection and Transition Measurements, Rev. Sci. Instrium, Sep. 1981, vol. 52, No. 9, pp. 1306-1310.

*Primary Examiner*—Eugene R. Laroche
*Assistant Examiner*—Robert J. Pascal
*Attorney, Agent, or Firm*—Roylance, Abrams, Berdo & Goodman

[57] ABSTRACT

The apparatus for detecting gases comprises a photoacoustic gas detector 35, in which the intensity-modulated absorbed test light beam 32' is converted into noise and detected by means of microphone 36. The photoacoustic gas detector 35 is acoustically decoupled from the gas collecting point 54 by a gas-permeable diaphragm 52 or a rigid, porous material 52'. The gas chamber 35' of photoacoustic detector 35 can be scavenged by means of supply lines 38, 38' and valves 56, 56'. It is advantageous to use a thermal source 32 intensity-modulated by phase lag. The signal is processed at microphone 36 by means of a N-path filter comprising cyclic switch 63 and R-elements 62, 65, 65'. The apparatus can be used for detecting $CO_2$ and CO.

43 Claims, 2 Drawing Sheets

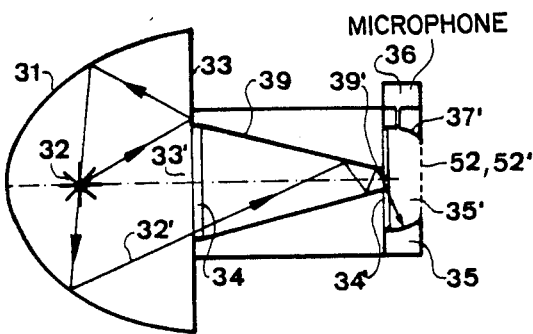
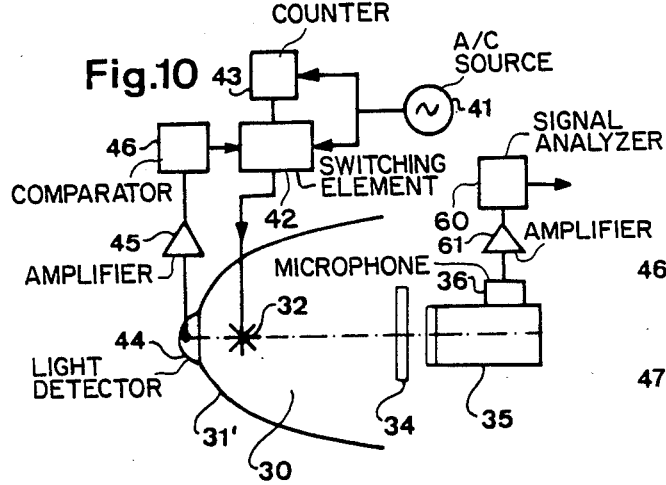
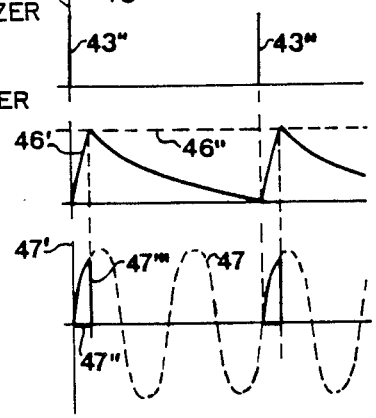
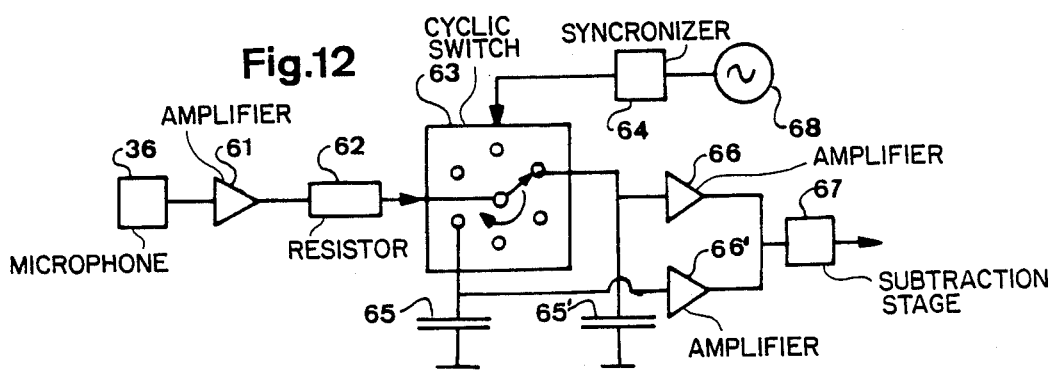

APPARATUS FOR THE PHOTOACOUSTIC DETECTION OF GASES

FIELD OF THE INVENTION

The present invention is in the field of photoacoustic spectroscopy, acoustics, electronics and biosensor technology, and relates to an apparatus for detecting gases, including vapors dissolved in a liquid or mixed as condensate therewith. The gases can come from a biological reaction. The detection of the gases or vapours is based on the photoacoustic effect. An apparatus for detecting the corresponding electric signals is also described.

BACKGROUND OF THE INVENTION

There is without doubt considerable interest in simple apparatus for the reliable, selective detection of gases. Such gases can either be present directly as components of a gaseous mixture, such as air, or from a biological tissue, such as from a photosynthesizing plant leaf, or e.g. from a biological reaction. The biologically active systems can be living organisms, such as bacteria or biologically active extracts from biological samples, e.g. enzymes. The biologically active system is generally suspended in the liquid, namely water, or is immobilized on a carrier, e.g. a plastic, metal or glass surface.

An apparatus for the detection of gases dissolved in a liquid and formed e.g. by a biological reaction are described in Swiss Patent Application 572/84-1 of Feb. 7th 1984.

However, there are also microbiological systems such as enzymes and bacteria, which are reactive with the air. They either can be present in aerosol form, or, as stated, can be immobilized on a carrier.

If a substrate is added, which substrate can be decomposed by the biologically active system, then gaseous products can form. The gas produced is then a measure of the activity of the biological organism or the bioactive extract.

On the basis of the gas production, information can also be obtained on the concentration of the substrate. As in general biological reactions take place in a highly specific, selective manner, the possibility arises of obtaining, on the basis of the determination of the gases produced, clear and qualitative information on the substrates. Equipment operating according to this principle are covered by the term biosensors. The problem arises of detecting the reaction product, i.e. to produce an electric signal, whose quantity is related to the concentration of the dissolved gases.

For the detection of gases, it is possible on the one hand to use chemical methods, such as titration, calorimetry, gravimetric determination of precipitates, etc. and on the other hand purely physical methods, such as optical spectroscopy, mass spectrometry, etc.

Admittedly chemical methods are generally simple with regards to the equipment, but as a result of the complexity of the reaction sequence, e.g. the reagent supply, separation by filtration, etc., they are less suitable for automatically controlled measurements.

It may also be necessary to carefully separate the apparatus where the biological decomposition takes place, the so-called bioreaction from the chemical reactor, in order to prevent poisoning by chemicals of the bioactive, systems.

Another unfavourable point in chemical determinations is the time taken for the chemical reaction and for the test specimen or sample preparation.

Therefore preference is given to physical determination of gaseous biological reaction products. Unfortunately corresponding methods are usually linked with high equipment expenditure, particularly in the case of spectroscopic methods. However, it must be stressed that optical-spectroscopy methods are characterized by high reliability and selectivity, so that further comment will be made thereon.

The following spectral ranges are worthy of consideration for the optical-spectroscopic detection of biological products: ultraviolet and visible range (180–800 nm), and infrared range (0.8 to 20 $\mu$m).

In the ultraviolet and visible spectral ranges, the molecules in question generally have broad-band and less specific absorption structures. Thus, apart from exceptions, this spectral range is generally not very important. However, with regards to selective detection, considerable importance is attached to the infrared spectral range. Particularly in the range of 10 $\mu$m, many organic molecules have very specific absorption lines (fingerprint range).

An important disadvantage of infrared spectroscopic analytical method is that it is scarcely possible to perform tests in aqueous solutions, because the water has very strong, all-surpassing absorption lines distributed over the entire important infrared spectral range. Thus, for infrared tests, organic substances are usually dissolved in organic solvents or processed to suspensions. This possibility is generally unsuitable for investigating substances obtained from biological reactions, because, apart from a few exceptions, biological reactions take place in water and consequently the reaction products also exist in the form of an aqueous solution or suspension.

Thus, infrared spectroscopic detection methods almost unavoidably require separation of water from the reaction product. The latter can be dried and either, as stated, mixed with an organic solvent or can be mixed with an inorganic salt, such as KBr, and pressed into a pill.

The separation of the reaction product from water is time-consuming and complicated. This method would certainly be unsuitable for automatic detectors. As a result of the gas/liquid equilibrium, it would be relatively easy to separate a reaction product with a high vapour pressure, at least partly from the water. It is merely necessary to prevent the problems caused by water vapour.

There are two different methods available for optical spectroscopic detection of gases and vapours, on the one hand the direct extinction method and on the other the photoacoustic method.

The extinction method comprises measuring the light intensity before ($I_o$) and after ($I$) the gas absorption cell. Conclusions can be drawn regarding the concentration of the light-absorbing gas from the difference ($I_o-I$) of the two measurements. This method permits analysis in flowing gas. However, it is only suitable for determination of relatively high gas concentrations, unless very considerable cell lengths or multiple reflection cells can be accepted. However, in the latter case it is necessary for the incident light beam to be narrowly focused (although if necessary the divergence of the beam can be counteracted by a special mirror shape), and on the other hand the mirror system must be very accurately adjusted. Thus, multiple reflection cells are generally very complicated and costly.

If a reliable measurement is to be performed, then the light attenuation (Io-I)/Io must move within certain limits. A lower limit of 1% and an upper limit of 99% means that no great demands must be made on the stability of the light source and light detectors. The optical path length of the gas cell must be adapted to these limits.

For the detection of low concentration, atmospheric gas contaminants, such as CO or $CH_4$, the photoacoustic gas detection method has proved very satisfactory. This method consists of the detection by a microphone of pressure changes, which occur in a gaseous mixture on absorbing monochromatic, intensity-modulated light (mainly infrared radiation) due to a gas component, such as is described in the article by L. G. Rosengren (Appl. Optics, 14, 1968, 1975. For this purpose, generally intense, matchable infrared lasers, together with highly sensitive capacitor microphones are used. The method is very sensitive, e.g. L. B. Kreuzer, J. App. Phys, 42, 1934, 1974 was able to detect methane in nitrogen in a concentration of 10 ppb (10E-8) with the aid of a 16 mW laser.

On accepting much lower requirements regarding the sensitivity of gas detection, considerable simplification of the detection system is possible. In particular the costly, matchable infrared laser can be replaced by a simple system having an incandescent body and a narrow-band interference filter. Admittedly of late M. J. D. Low and G. A. Parodi, Infrared Phys., 20, 333, 1980 have described an infrared spectrometer based on the photoacoustic effect, in which an incandescent pin is used in place of the laser. However, as a result of its weak intensity, this source has not proved very satisfactory when combined with a grating monochromator for a photoacoustic infrared spectrometer. The replacement of the grating monochromator by an interference filter leads to advantages regarding the intensity measurement, but the flexibility and accuracy suffer.

Our own measurements have shown that very good results can be obtained in connection with the sensitivity thus, when using a thermal radiation source mechanically modulated at 5.6 W electric power and an interference filter as the monochromator (light power 2.6 E-5 AVW cm) $CO_2$ could be reliably detected in $N_2$ with a concentration of 1.5 ppm, as described in the article by O. Oehler, D. Marek and A. Fries, (Helv. Phys. Acta, 54, 631, 1981).

In a certain sense it is surprising that this method can operate without lasers. However, it is pointed out in this connection that in general laser radiation can only excite a single sharp rotational line of the complex vibration-rotation spectrum of a low molecular gas. The combination of a thermal radiation source and interference filter makes it possible to excite the complete absorption band system. As the photoacoustic effect is proportional to the total light power absorbed, it is interesting that a good result can still be obtained when using a weak intensity broad-band light source.

However, it must be borne in mind that the light can be concentrated very efficiently in a detector gas cell of small volume V, because one third L/V of the light power L absorbed in the cell is decisive for the size of the photoacoustic signal. The proportionality between the photoacoustic cell and the light intensity mesns that high demands cannot be made on the intensity stability of the light source, contrary to the situation in the extinction method.

In one category of gas analyzers based on the photoacoustic effect, the infrared laser has been successfully replaced by an incandescent body. These consist of the so-called, non-dispersive photoacoustic gas analyzer systems, of which numerous different constructions exist. Reference is made in this connection to German Pat. No. 2751047 of O. H. Blunck and No. 2748089 of U. Deptolla and F. Fabinski.

In the case of these non-dispersive systems, it is not the absorptive light quantity absorbed by the gas component adapted to the filter which directly gives rise to the microphone signal, but instead the difference of the light attenuation between the sample gas and a reference gas is selectively measured by means of a split up light beam. The gas-selective light intensity difference measurement is determined with a photoacoustic difference measuring cell, which is filled with the gas of the component being tested. This construction has the advantage that no monochromatic radiation is required. However, a corresponding apparatus only makes it possible to determine a single gas type. Moreover, such systems have a complicated construction, because in conjunction with the difference signal measurement, the two light beam fractions have to be very accurately compensated.

In summary it can be stated that optical-spectroscopic gas detection methods almost always require considerable effort and expenditure. However, the intention is to provide a simple detection apparatus for gases dissolved in liquid and this requirement is met by the photoacoustic measuring principle using a thermal source, as described in the article by O. Oehler and D. Sourlier (Helv. Phys. Acta, 55, pp. 594-597, 1982).

The photoacoustic effect is based on the fact that measurement takes place through the sound field formed in the gas cell through the absorption of intensity-modulated light radiation. Thus, a photoacoustic measuring apparatus is sensitive from the outset to acoustic disturbances. It is therefore unavoidable that corresponding sound-attenuating measures are taken.

During the measurement it must on the one hand be ensured that the light absorption-resulting sound signal is not weakened by the escape of gas from the photoacoustic cell and on the other hand the penetration of external space sound, which could increase the noise level of the measurement, is prevented.

If operation takes place with a high modulating frequency, it is possible to make do with simple flow-resisting elements, such as diaphragms and the like. However, it is unavoidable in the case of low modulating frequencies to use efficient sound attenuating means. However, great importance is attached to the operation of a photoacoustic gas detector at low modulating frequencies, because corresponding equipment involves little expenditure. If necessary, the light source can even be thermally modulated by switching the light source current on and off, which certainly represents a simple and reliable solution, compared with light interruption, with a mechanical aid, e.g. a rotating diaphragm. Operation normally takes place with completely closed photoacoustic gas detector cells.

Very simple solutions for the acoustic separation of the leads are described in the patent applications of Oehler et al., PCT/CH82/00026 and PCT/CH83/00080. They are based on a hydrodynamic acoustic decoupling. They are based on the fact that air and liquid media have very different acoustic stiffnesses (h=E, E=modulus of elasticity and h=density) and consequently the acoustic power matching at the gas—liquid and liquid—gas interfaces is very poor. In the human ear, e.g. where the problem in question arises with sound transmission from the outer ear to the perilymph of the inner ear, the necessary good power matching is ensured by the auditory ossicle within the middle ear. The different acoustic stiffnesses of air and perilymph is taken into account by a mechanical transmission (transmission ratio 60:1).

One acoustic separating apparatus comprises a liquid-filled, gas washing bottle-like dipping tank being fitted on either side of the photoacoustic gas detector. By means of a limited overpressure, which can e.g. be produced by means of a diaphragm pump, gas is blown through the liquid and consequently the exchange of the gas in the cell is accomplished. Admittedly no photoacoustic measurement can be performed during this process. The typical noise occurring on blowing the gas through the liquid would disturb the measurement too much.

On switching off the pump, the liquid level stabilizes, so that acoustic decoupling is ensured. There is an acoustic attenuation of 40 to 55 db in the case of measurements in the 10 to 100 Hz frequency range.

A second construction of the acoustic separating apparatus comprises the separating liquid being held in narrow tubes by capillary forces. Under a limited overpressure, the liquid is expelled from the capillary tubes which ensures the gas exchange. On switching off the pump, the liquid flows back into the capillary tubes the valve being acoustically closed. The acoustic attenuation of this apparatus is high and values of 60 to 70 dB have been obtained in the frequency range of 10 to 100 Hz.

It is conceivable to suck off the medium to be detected, i.e. gas or vapour, and to supply it to the photoacoustic cell for optical-spectroscopic testing. Consideration can indeed be given to this method if the connecting means between the gas removal or gas collecting point and the detection cells can be made geometrically small, so that a rapid gas transfer is possible. However, a very close contact is sought, between the removal/collecting point and the gas detector.

Account has been taken of this in a further construction relating to acoustic separation in the photoacoustic cell. This third construction is described in Swiss Patent Application 572/84-1 of Feb. 7th 1984 and 2594/84 of May 28th 1984. The inner area of the photoacoustic gas detector is separated from the outside, constituting the gas collecting point, by a gas-permeable diaphragm. Despite its gas permeability, such a diaphragm provides a sufficiently large acoustic attenuation to ensure a photoacoustic measurement.

This arrangement leads to a particularly simple gas detector, in that the gas exchange between the gas collecting point and the photoacoustic gas detector takes place purely passively by gas diffusion through the diaphragm, instead of requiring a pump.

It has proved advantageous if no light from the test beam strikes the gas-permeable diaphragm. In the case of diaphragm illumination, even when an absorbing gas is absent in the detector room there is a large photoacoustic signal, which can be attributed to the light absorption in the diaphragm.

It is also pointed out that a gas-permeable diaphragm is not an ideal acoustical resistance, particularly if operation is to take place at low light modulating frequencies. In accordance with the calculations, with a 0.9 $cm^3$ capacity photoacoustic cell separated by a gas-permeable diaphragm with a diameter of 0.5 cm, acoustic attenuation factors of 5 to 30 dB were obtained at 5 Hz, as a function of the diaphragm type.

Significantly better results can be expected on replacing the thin, flexible, gas-permeable diaphragm by a rigid, porous material such as e.g. a sintered product.

Thus, the photoacoustic signal is generally small and very noisy. These disadvantages can be counteracted by using an intense, intensity-modulated light source, as well as a very low-band electronic filter.

As the diaphragm-decoupled, photoacoustic gas detector is an extremely simple and inexpensive gas detection means, the light source and the control thereof, as well as the signal detection electronics must be made correspondingly simple. Such means are described in Swiss Patent Application 4249184-3 of September 6th 1984.

Patent application PCT/CH 83/00080 already describes a very efficient thermal light source. The hereinafter described invention is based on a photoacoustic gas detector, which is acoustically separated from the gas collecting point by a gas-permeable diaphragm or by a rigid porous material, such as e.g. a sintered product, as well as electronic means for the intensity modulation of the light source and for detecting the microphone signal.

SUMMARY OF THE INVENTION

Objects of the present invention are to provide an apparatus enabling gases or vapours, which can escape from a liquid or a solid material, to be detected in a very simple and inexpensive manner by the photoacoustic method.

A preferred embodiment is intended to detect the gases or vapours from a biological tissue or from a biological reaction.

The foregoing objects are obtained by an optical detection apparatus for selectively detecting gases, including vapors, comprising a light source located within optical collector defining an optical path, a gas collecting cell in the optical path including a photoacoustic gas detector for generating signals representative of gases detected in the gas collecting cell, a monochromator in the optical path between the light source and the gas collecting cell, and a gas exchanger for supplying gases to and discharging gases from the gas collecting cell. The gas exchanger includes an acoustically attenuating element at a gas collection point which is continuously permeable to gases and is exposed to medium to be measured at the gas collection point. Alternatively, the gas exchanger includes alternately closable valves. A signal processor is coupled to the detector and analyzes signals of the detector.

The foregoing objects are also obtained by a method of selectively detecting gases, including vapors. The method comprises the steps of emitting light from a light source located within optical collector into a gas collecting cell in the optical path of the light source, generating signals representative of gases detected in the gas collecting cell by a photoacoustic gas detector, opening the photoacoustic detector to surrounding gases though an acoustically attenuating element which is continuously permeable to gases so that the surrounding gases permeate the photoacoustic gas detector, and analyzing signals generated by the photoacoustic gas detector with a signal processor coupled to the photoacoustic gas detector.

Other objects, advantages and salient features of the present invention will become apparent from the following detailed description, which, taken in conjunction with the annexed drawings, discloses preferred embodiments of the present invention.

BRIEF DESCRIPTION OF THE DRAWINGS

Referring to the drawings which are a part of this disclosure:

FIG. 9 is a graphic representation of an optical detection apparatus according to an embodiment of the invention which prevents illumination of the gas-permeable, acoustically attenuating elements;

FIG. 10 is a graphic diagram illustrating an apparatus for thermal modulation of an incandescent body by a phase lag circuit;

FIG. 11 is a graph illustrating time patterns of the operation of the phase lag circuit of FIG. 10; and FIG. 12 is a diagram of the circuit for detecting and analyzing very noisy microphone signals containing a periodic component of an N-path filter.

DETAILED DESCRIPTION OF PREFERRED EMBODIMENTS

Figure 1:
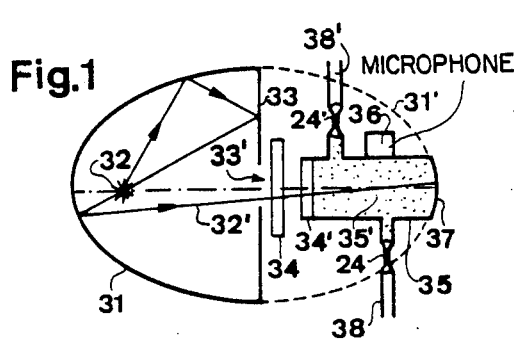
FIG. 1 is a graphic representation of a simple photoacoustic detector for gases with acoustic decoupling elements and a thermal light source.

FIG. 1 shows a simple gas measuring apparatus, based on the photoacoustic principle and having a thermal source 32. The operation of this apparatus is described hereinafter. The essential component is the optical collecting means, comprising an ellipsoidal concave mirror 31, in whose one focal point is located an optically partially transparent thermal source 32, e.g. a coiled-up filament.

In the centrally bisecting plane of the ellipsoidal surface 31 is provided a counter-reflector in the form of a plane mirror 33, which reflects back the instant light either directly or indirectly on the source 32. This process is repeated until the light beam approaching the major axis is finally decoupled by the central light opening 33' in main mirror 33. The focused light beam 32' initially strikes an optical band pass filter 34 and finally to window 34' in the photoacoustic detector 35. If the light beam 32' is intensity-modulated, which is e.g. possible through the alternating switching on and off of source 32, then the radiation absorbed by the gas in the photoacoustic gas detector 35 leads to periodic pressure fluctuation, which are detected by microphone 36. For lengthening the light path, it is appropriate to place a flat or curved light reflector on the rear wall of the photoacoustic gas detector 35. It is possible to use with particular advantage a concave mirror 37, shown in FIG. 1, which is adapted to the shape of the substituted ellipsoid half 31'. As a result, the non-absorbed component of the radiation striking the photoacoustic gas detector 35 is reflected back into the ellipsoidal reflector 31, 33 without varying the optical path. This leads to an increase in the optical efficiency of the optical collecting means.

The filling of the photoacoustic gas detectors 35 with the gas to be detected takes place by means of the gas supply or removal connections 38, 38' and the light detectors 24, 24' filled with the confining liquid. The operation of these gas exchange means, also serving for acoustic decoupling purposes has already been explained.

Figure 2:
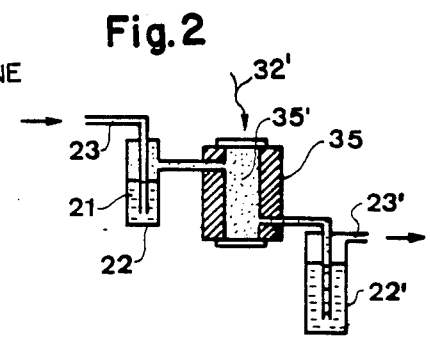
FIG. 2 is a graphic illustration of an acoustic decoupling device based on a hydrodynamic principle.

FIG. 2 shows the aforementioned acoustically decoupling gas exchange means, with gas washing bottle-like dipping tanks 22, 22' filled with the confining liquid 21. The gas exchange in the photoacoustic detector takes place by means of the gas supply and discharge connections 23, 23'.

Figure 3:
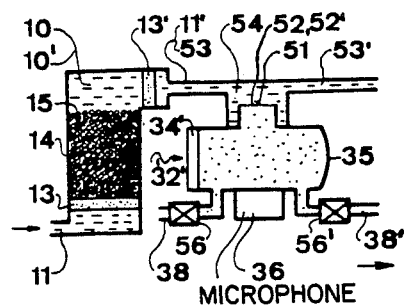
FIG. 3 is a graphic side elevational view of a biosensor comprising a combination of a bioreactor and a photoacoustic gas detector wherein a gas-permeable diaphragm performs a liquid-gas interface.

FIG. 3 shows the combination of a chemical reactor 10', particularly a bioreactor 10, and a photoacoustic gas detector 35. Reactor 10' and detector 35 are interconnected via the gas passage 45, the latter being provided with a liquid-separating, gas-permeable diaphragm 52.

The bioreactor 10 functions as follows. A liquid, e.g. water, contained in the starting substance to be analyzed in dissolved or suspended form, is supplied via the reactor feed connection 11 to a gas or vapour-producing element 10', e.g. the bioreactor 10. The liquid flow is maintained either hydrostatically by a liquid level difference, or by means of a pumping device. The liquid, which can contain a substrate in dissolved or suspended form, passes into the reaction chamber 14 through the permeable reactor separation surface 13, which can e.g. comprise a sintered glass plate. The bioactive substance, e.g. bacteria or one or more enzymes, is located in reaction chamber 14. The bioactive substance is either freely movable in the reactor chamber, or is immobilized in a suitable form on a support, e.g. porous glass balls 15, plastics, ceramic material or metal. The immobilization of the bioactive system of a support is advantageous, because the fixed substances are more stable and have a longer life than the free substances. In addition, a reliable separation of the bioactive substance in the case of simultaneous efficient circulation of the liquid through the reactor separating surface 13, 13' would be problematical. The biological decomposition of the substrate to which the liquid is added, takes place in reactor chamber 14. As a result of the partial or complete biological decomposition, the biological reaction products are formed e.g. as dissolved gases, such as $CO_2$, $NH_3$, $H_2$.

The reaction products leave the reactor 10' with the liquid through the other reactor separating face 13' via reactor discharge connection 11'.

As biological and chemical reactions have a considerable thermal dependence, it is appropriate to thermostatically control the reactor chamber. The temperature can be maintained constant e.g. with a liquid jacket.

This gas or vapour-enriched liquid then passes via the feed connection 53 to the gas collecting point 54, which is connected to the photoacoustic gas detector 35 via the diaphragm-covered passage 51, which can alternatively be provided with a rigid porous material 52'. The gas or vapour-depleted liquid leaves the gas collecting point 54 via discharge connection 53'. The operation of the gas-permeable diaphragm 52, in combination with the gas detector 35' in the manner shown in FIG. 3, can be described in the following way.

The connection of the photoacoustic detector 35 via the liquid-separating, gas-permeable element 52, 52', e.g. the gas-permeable diaphragm 52, is appropriate, because as a result of the aforementioned difference between the acoustic impedence of the two media, a liquid—gas interface represents a certain acoustic decoupling. However, even a very thin, gas-permeable diaphragm 52, fitted to the passage 51 of the wall of the photoacoustic cell leads to very efficient acoustic decoupling, even in the case of low light modulating frequencies (4 to 20 Hz).

The liquid-filled gas collecting point 54 is e.g. positioned above the gas-containing photoacoustic gas detector 35 and is connected to the latter via gas passage 51. As stated, liquid—gas separation e.g. takes place through the gas-permeable diaphragm 52. However, the gas-permeable diaphragm 52 can be omitted if the geometry and pressure conditions in the photoacoustic gas detector 35 and gas collecting point 54 are appropriately chosen, so as to prevent the penetration of liquid through gas passage 51. The gas exchange at gas passage 51 is then admittedly of an optimum nature, but the acoustic decoupling of the photoacoustic gas detector 35 is in this case problematical.

If the photoacoustic detector 35 is not provided with gas feedlines, following a liquid exchange via connections 53, 53', gas concentration determination cannot take place until equilibrium has been reestablished between the gas and liquid phases. However, if exchange can take place between the photoacoustic gas detector 35 via connections 38, 38' and valves 56, 56', if necessary of a hydrodynamic nature of detectors 24, 24' or tanks 22, 22', then there is no need to wait for setting the gas-liquid equilibrium. If e.g. the optical absorption spectrum of the scavenging gas does not interfere with that of the test gas to be investigated, then following the disconnection of the scavenging gas flow, conclusions can be drawn in a reliable manner regarding the concentration of the test gas in the liquid from the rise of said gas partial pressure.

The photoacoustic measuring process with the aid of microphone 36 has already been described, cf. FIG. 1. The intensity-modulated light coupled in through window 34' need not necessarily come from a thermally-modulated radiator or source 32 with an elliptical reflector 31, 33 according to FIG. 1 and it would also be possible to use a different infrared light source, e.g. a thermal light source, together with a different reflector, or e.g. a laser. With regards to the simplicity and efficiency an appropriate solution is however provided by the elliptical reflectors 31, 33 of FIG. 1, but in which the thermal circulation of source 32 is replaced by a mechanical modulation device.

Figure 4:
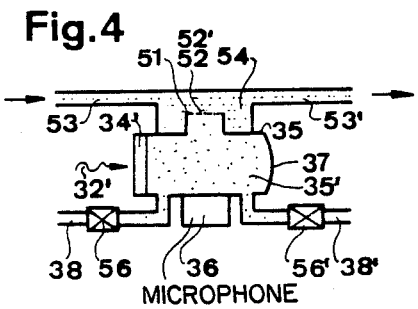
FIG. 4 is a graphic side elevational view of the separation of the gas removal point from the photoacoustic gas detector by a gas-permeable diaphragm or a rigid-porous material.

FIG. 4 shows the gas detector with the acoustically attenuating, gas-permeable diaphragm 52 or the rigid, porous material 52', e.g. sintered material. The apparatus constitutes a slight modification of the aforementioned apparatus and as shown in FIG. 3. Measurements and calculations have shown that a gas-permeable diaphragm 52 alone provides an adequately good acoustic decoupling for photoacoustic measurements, even without its simultaneous function as a gas-liquid separation means. It is therefore possible to reliably detect only the gas components dissolved in a liquid, but also those present in a gaseous mixture, e.g. by means of a diaphragm-separated, photoacoustic detector 35. However, it is pointed out that the geometry of diaphragm 52 or the rigid, gas-permeable material 52', or the capillary structure thereof has a very significant influence on the usability as an acoustically decoupling element 52, 52', 73, 81 (FIG. 7) (FIG. 8). An asymmetrical diaphragm, which is provided with a 10 nm thick separating film, which in turn, has two nm capillaries with a density of $4 \times 10^{12}/cm^2$, e.g. provides an acoustic attenuation of 34.7 dB, a value which is quite sufficient for the set requirement. The gas detector of FIG. 4 differs from that of FIG. 3 in that it is not necessarily a liquid, which increases the acoustic decoupling of the photoacoustic gas detector 35 which is present at the gas collecting point 54 and instead a gas can also be present, which can pass through the gas-permeable diaphragm 52 or the rigid, porous material 52'. Information concerning the test gas concentration at the gas collecting point 54 is e.g. obtained from the equilibrium—test gas concentration in the photoacoustic detector 35'. As has already been described, it is possible to indirectly determine the test gas concentration. To this end, e.g. initially the photoacoustic gas detector 35 is scavenged with a gas which does not interfere optically with the gas to be measured. Then, as stated, the gas concentration at the gas collecting point 54 is determined on the basis of the test gas concentration rise in the photoacoustic gas detector.

The reaction products, which are e.g. obtained from a biological reaction, are not passed through a carrier liquid and are instead passed through a carrier gas to the gas collecting point 54. Biological gas reactions are possible, if the necessary moisture is ensured in bioreactor 10. The bioreactor can also contain a liquid, but it is not necessarily the liquid which passes to the gas collecting point 54 and instead it may only be the gaseous reaction products, and, if necessary, a carrier gas.

Figure 5:
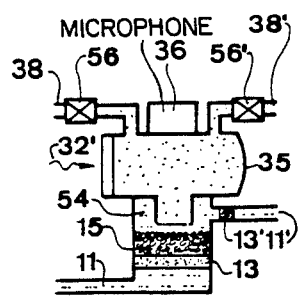
FIG. 5 is a graphic side elevational view of a biosensor comprising a gas-scavenged bioreactor and a photoacoustic gas detector.

FIG. 5 represents a slight modification of the means of FIGS. 3 and 4, in that the chemical or biochemical reaction takes place directly at the gas collecting point 54, i.e. reactor 10' and gas collecting point 54 are combined. A further possibility is that the chemically active, e.g. bioactive material is not immobilized on a carrier 15 and is instead applied directly to the acoustically attenuating, gas-permeable element, e.g. the gas-permeable diaphragm 52.

Figure 6:
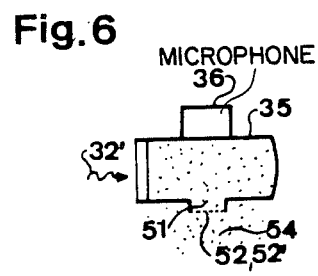
FIG. 6 is a graphic side elevational view of a simple photoacoustic detector for gaseous components in which acoustic decoupling is provided by a gas-permeable diaphragm or a rigid, porous material.

FIG. 6 shows a simple detection means for components of the gas surrounding the photoacoustic gas detector 35, e.g. ambient air. The acoustic decoupling of the photoacoustic gas detector 35 from the surrounding gas chamber representing the gas collecting point 54 is once again ensured by acoustically attenuating, gas-permeable element, e.g. a gas-permeable diaphragm 52 at gas passage 51. If no scavenging gas can be passed through the photoacoustic gas detector, as is e.g. shown in FIG. 4, then the gas concentration determination in gas detector 35 is very slow, due to the slow, diffusion-caused setting of the gas concentration equilibrium. However, as can be gathered from FIG. 6, the apparatus in question has a very simple construction. The disadvantage of the measurement inertia can be counteracted by miniaturizing the photoacoustic cell, i.e. by reducing the volume.

Figure 7:
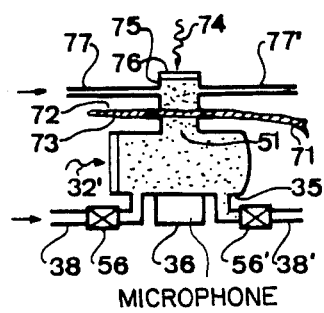
FIGS. 7 and 8 are graphic side elevational views of open photoacoustic measuring apparatus acoustically decoupled from the ambient environment by the material being measured.
Figure 8:
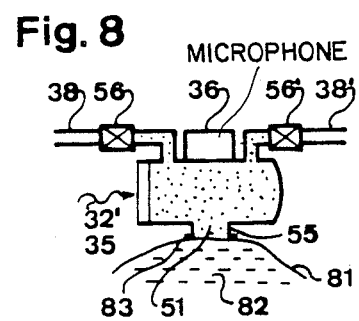

FIGS. 7 and 8 show further and in part biological uses. In the case of the use, as shown in FIG. 7, the surface of a photosynthesizing, plant or vegetable leaf 71, which is pressed against the passage 51 of photoacoustic detector 35, simultaneously acts as an acoustically decoupling, gas-permeable element. As no additional acoustic decoupling element is required, which necessarily forms a further gas diffusion barrier, the gas exchange in this arrangement is very good. Preferably the leaf is arranged in such a way that its top surface 72 with the underlying chlorophyl-containing leaf cells, is remote from the photoacoustic detector 35, whilst the bottom surface 73 of the leaf with the slit openings faces said detector 35. Through the controlled irradiation of visible light 74, the leaf is excited to photosynthesis and consequently the photosynthesis gas exchange through the slit openings is activated. These gases are analyzed in the photoacoustic gas detector 35 by means of the monochromatic measurement light beam 32'.

For maintaining quasi-constant conditions regarding the gas partial pressure, it is appropriate to scavenge the photoacoustic gas detector in a constant manner via connections 38, 38' and valves 56, 56' and to only briefly interrupt the gas flow during the measurement. The gas flow interruption is not necessary if an adequate acoustic decoupling of the gas feed lines 38, 38' and a sufficiently constant flow are ensured, so that the photoacoustic measurement is not significantly disturbed. It is also advantageous if the top surface of the leaf is exposed to a quasi-constant gas atmosphere. This can e.g. be achieved by means of a leaf covering vessel 75, which is provided with a window 76 and gas supply and discharge connections 77, 77'.

FIG. 8 shows a photoacoustic gas detector 35, which has a gas passage opening 51 constructed as a connecting piece 55. The latter is terminated by a pressed-on, acoustically decoupling, gas-permeable element 81, which in turn forms the surface of the material being measured 82. A good termination of connecting piece 55 is ensured by an additional seal 83.

The material being measured 82 can be an organism or part thereof and the gas-permeable element 81 can be the skin thereof. Material 82 can also be an enveloped lifeless object, the envelope, e.g. a plastic foil representing the acoustically decoupling, gas-permeable element. For rapid and reliable measurements, it may be advisable to scavenge the photoacoustic gas detector 35, following the sealing of connecting piece 55 by material 82, via gas lines 38, 38' and valves 56, 56'. The optical absorption spectrum of the scavenging gas must not interfere with that of the gas being tested.

FIG. 9 shows an optical apparatus 31, 32, 33, 37', 39, which substantially prevents the illumination by the test light beam 32' of the acoustically attenuated gas-permeable element, e.g. gas-permeable diaphragm 52.

As has already been stated, it has proved advantageous in connection with gas-permeable diaphragms 52, for them to be exposed to the minimum possible extent to the light beam 32'. Otherwise there is a large zero signal, i.e. a large photoacoustic signal can be observed in the absence of an absorbing gas in gas detector 35.

It is also necessary to ensure that the test light beam 32' is concentrated as efficiently as possible on a small detector volume V, 35', because the photoacoustic signal is proportional to the density L/V of the radiant power L absorbed in the detector. The two requirements of keeping the gas-permeable element 52, 52' 71, 81 dark and simultaneously ensuring a light concentration can e.g. be satisfied by a conical light pipe 39.

With the aid of a tubular, conical inner reflector 39, as shown in FIG. 9, it is possible to narrow a light beam. This narrowing leads to a significant increase in the divergence of the ray bundle at the narrowed light pipe outlet 39'. The latter characteristic of the conical light pipe makes its use for light concentration problematical in many cases, e.g. it is a question of concentrating radiation on a small detector surface. The beam cross-section at the light pipe outlet 39' is very narrow, but due to the considerable divergence only a small part of the emitted light can be brought onto the detector surface positioned just in front of opening 39'. However, this is very much desired here, because the test light beam 32' should as far as possible be kept away from the acoustically attenuating gas-permeable element 52, 52', 71, 81, because the latter can be positioned opposite the narrowed light pipe outlet 39' and gives a very small, volume photoacoustic gas detector 35.

The description of FIG. 1 referred to the advantage of a reflector 37 fitted to the rear wall of the photoacoustic detector 35. This permits a return of the test light beam into source 32. In the same way, it can be achieved by means of a spherical reflector 37', that the light emitted by the light pipe opening 39' under a large angle is reflected back into the region of source 32. Apart from the lengthened absorption light path, the reflector surface 37' of photoacoustic detector 35 leads to an increase in the efficiency of the optical apparatus. A disadvantage of the optical apparatus 31, 33 of FIG. 1 is the fact that the light emitted by opening 33' is not homogeneous. The reason for this is the partial covering of the light path by the partially transparent source 32, e.g. the coil. As is known, the lack of homogeneity in a light beam can be eliminated by multiple reflection in the light pipe. The aforementioned conical light pipe 39 is also advantageous in this respect.

For financial reasons, it would be advantageous if the optical band pass filter 34 fitted to the narrowed light pipe outlet 39' (small diameter) when using an interference filter, this is hardly possible due to the large divergence of the test light source 32'. It is therefore appropriate to fit the optical band pass filter 34 to the wide opening of light pipe 39.

FIG. 10 shows a light source comprising reflector 31, and the light source 32 designed as a thermal source, together with the thermal modulation thereof by phase lag means at 41–46.

This is based on a periodic electric signal, which is taken from an alternating electric source 41, e.g. via a transformer, directly from the mains. A fast electronic switching element 42 periodically removes a portion from the periodic signal, passes it to the thermal source 32 and brings about a modulation of the radiation intensity. Switching element 42 is operated either at the fundamental frequency or at a subharmonic of the fundamental frequency means that it is possible to largely prevent crosstalk from the electric source 41 (hum when using the mains as the power supply) to the microphone 36 (possibly also light detector 44). The subharmonic is produced by a frequency divider 43, e.g. a counter.

To reduce stressing on source 32 and consequently to prevent the premature failure thereof, the switch 42 is advantageously switched on during the zero passage of the voltage of source 41.

Disconnection either takes place after a predetermined time (phase lag length 47" according to FIG. 11) or e.g. on reaching a predetermined source temperature 46". The latter is e.g. made with the aid of light detector 44. The detector signal raised in amplifier 45 is compared in comparator 46 with a desired value 46" in FIG. 11. With the aid of the output signal of comparator 46, switch 42 is finally reset.

The optical collecting device can be constituted by device 31, 32 with the semi-ellipsoidal reflector 31, as shown in FIG. 1, but it is also possible to use a different optical collecting device 31'.

FIG. 11 shows the operation of the temperature-controlled phase lag device according to FIG. 10, in which 43' is the time sequence of the source switching pulses 43" of frequency divider 43 and 46' the time configuration of the source temperature within a predetermined desired temperature valve 46". 47' is the time configuration of voltage 47 of source 41 (broken line), whilst the signal 47" supplied to source 32 is indicated by the continuous line.

FIG. 12 shows the switching principle of the N-path filter, which is suitable for detecting and analyzing the microphone signal. The very noisy signal containing a small periodic component of an acoustic detector, e.g. microphone 36, is amplified in selective amplifier 61, and as a result of its low pass characteristics is free from low and high frequency spurious signals. The signal is subsequently supplied to a signal analyzer 60, having parts 62-68, in which the periodic signal component processed. The latter consists of the period of the useful signal (i.e. the periodic component of the amplified detector signal) being subdivided into a plurality and at least two time slots. The synchronization of the time slot-subdivided element 63 is carried out by means of a reference signal 68, which is in turn synchronized with the periodic signal component produced in the detector. A signal averaging takes place in at least one of the time slots. The several signal mean values corresponding to the different time slots can e.g. be processed by subtracting and supplied to a recording or indicating element.

Time slot subdivision is e.g. brought about by a cyclic switch 63 which, controlled by means of the frequency synchronizer 64, runs synchronously with the periodic detector signal component to be analyzed. Signal averaging can take place in simple manner with RC-elements, which e.g. comprise a common ohmic resistor 62, as well as capacitors 65, 65', the latter being appropriately of the same size. The RC-time constants are to be made large compared with the time slot lengths. The resulting voltages on the capacitors 65, 65', '... become practically free from noise and are equivalent to the periodical parts of the microphone signals. The voltages are measured at capacitors 65, 65' via amplifier stages 66, 66', whose input currents bring about negligibly small voltage drops at resistor 62. The sought periodic signal can be obtained from comparison measurements of the voltages at several capacitors 65, 65', etc.

In FIG. 12, e.g. the voltages are processed at capacitors 65, 65' in the analog subtraction stage 67. The phase between the signal applied to light source 32 for modulation purposes and the signal at microphone 36 can be determined from the voltage ratio at capacitors 65, 65'. As the voltage ratio is substantially independent of the test signal size, but varies widely in the case of incomplete operability of source 32, optical collecting device 31, 31', 33, microphone 36 or the acoustic decoupling device 22, 22', 24, 24', 52, 52', e.g. the gas-permeable membrane 52, it is possible to use the phase position for function control purposes.

In summarizing, the apparatus according to the invention and its usability can be described as follows: The optical detector for the selective detection of gases is characterized in that the gas collecting cell is simultaneously a photoacoustic gas detector 35 and that the gas exchange device is an acoustically attenuating element which is always permeable for the gases, such as a gas-permeable diaphragm 52 or a rigid, porous material 52' and can be brought into contact with the medium located at the gas collecting point 54, such as a liquid or a solid material for measurement. The gas-permeable diaphragm 52, 73, 81 can be the enveloping boundary of the material 71, 72 for measurement.

The optical collecting device 31, 31', 32, 33 can be constructed in such a way that the test light beams 32' scarcely acts on the acoustically attenuating element 52, 52', 73, 81 which is always permeable for the gases. This requirement can e.g. be satisfied by using a conical light pipe 39 for producing a widely diverging test light beam 32', which can be positioned facing the gas-permeable elements. In this case, it is advantageous to give the photoacoustic gas detector 35 a concave mirror configuration 37', so that the radiation emitted by the light pipe opening 39' is returned to the latter.

The passage 51 between the photoacoustic detector 35 and the gas-permeable, acoustically decoupling elememnt 52, 5', 73, 81 can be extended in connecting piece-like manner 55.

The gas collecting point 54 can e.g. be connected to a gas and/or vapour producing element 10', which is possibly a chemical reactor 10, or the latter is itself arranged at the gas collecting point 54.

The chemical reactor 10 can contain a biologically active medium, which is immobilized on a support 15, e.g. on the gas-permeable diaphragm 52 or on the rigid, porous material 52'.

The optical detector for the selective detection of gases is further characterized in that apart from the use of a photoacoustic gas detector 35 and a gas-permeable, acoustically attenuating element 52, 52', 73, 81, which is alternately closable, an optical collecting device 31, 31', 33 is used, together with a source 32, whose intensity is thermally modulated by phase lag of a periodic electric signal 41. The phase lag can be brought about with a subharmonic frequency of the periodic electric signal 41 using the mains frequency as a basis. The intensity of source 32 can be checked by means of the phase lag length 47".

The phase lag length is also checked on the basis of the measurement of the intensity or temperature of the source 32 by means of a light detector 44. A detector for the selective detection of gases is also characterized in that signal processing means 61, 62, 63, 64, 65, 65', 66, 66', 67 are provided, which comprise a selective amplifier 61, and a signal analysis part 62, 63, 64, 65, 65', 66, 66', 67. The latter subdivides the period of the useful signal supplied by microphone 36 into at least two time slots, signal averaging being performed in at least one of these. The time slot subdivision can be realized with the aid of a cyclic switch 63, whilst signal averaging can be carried out by means of R(62)–C(65, 65') elements. The presence of at least two RC-elements makes it possible to determine the phase position between the modulating signal and the source 32 and the signal at microphone 36.

The test light beam 32' can come from an optical collecting device 31, 32, 33, which comprises a semi-ellipsoidal concave mirror 31 and a plane mirror counter-reflector 33. The latter is located at the central bisecting plane of the ellipsoidal surface 31. The radiation of the partly transparent thermal source 32 located at the inner focal point of the semi-ellipsoidal surface 31, is decoupled by the central light exit opening 33' of counter-reflector 33.

The apparatus can be used for measuring the gas surrounding the photoacoustic gas detector 35. The apparatus can also be used for measuring the gases present in the measuring material 82 in gaseous or dissolved form, which pass through the gas-permeable envelope 81 thereof. The apparatus can also be used for investigating photo-synthesis exchange gases of plant or vegetable organisms, in that a direct gas exchange is made possible between organisms 71 and the photoacoustic gas detector 35 by means of gas passage 51.

The apparatus can be used by feeding into reactor 10 a medium comprising or containing one or more substrates, which can be biologically reacted in reactor 10, so that one or more gases are formed, and they can be analyzed in the photoacoustic gas detector 35.

The apparatus can be used for the detection of toxic substances which reversibly or irreversibly block the biological reaction, in that, apart from the biologically reactive substrate or substrates, a substance is added to reactor 10 which blocks the biological reaction.

The knowledge of this phase position can be used for checking the function of source 32, optical colelcting device 31, 31', 33 of microphone 36 and the acoustic decoupling devices 22, 22', 24, 24', 52, 52', 73, 81.

The apparatus can be used for measuring $CO_2$ and/or CO. The apparatus can be used for specifically determining by means of the photoacoustic effect, the gas permeability and acoustic attenuation of gas-permeable elements 52, 52', 81, such as the gas-permeable diaphragms 52.

While various embodiments have been chosen to illustrate the invention, it will be understood by those skilled in the art that various changes and modifications can be made therein without departing from the scope of the invention as defined in the appended claims.

We claim:

1. An optical detection apparatus for selectively detecting gases including vapors, comprising:
    a light source located within optical collecting means defining an optical path;
    a gas collecting cell in said optical path, said gas collecting cell including photoacoustic gas detector means for generating signals representative of gases detected in said gas collecting cell;
    a monochromator in said optical path between said light source and said gas collecting cell;
    gas exchange means for supplying gases to and discharging gases from said gas collecting cell, said gas exchange means including an acoustically attenuating element at a gas collection point, said acoustically attenuating element being continuously permeable to gases and being exposed to a medium to be measured at the gas collecting point; and
    signal processing means, coupled to said detector means, for analyzing signals of said detector means.

2. An optical detection apparatus according to claim 1 wherein the medium to be measured at said gas collecting point is solid material.

3. An optical detection apparatus according to claim 1 wherein the medium to be measured at the gas collecting point is a liquid material.

4. An optical detection apparatus according to claim 1 wherein said acoustically attenuating element comprises rigid, porous and sintered material.

5. An optical detection apparatus according to claim 1 wherein said acoustic attenuating element comprises a gas permeable diaphragm.

6. An optical detection apparatus according to claim 5 wherein said permeable diaphragm is an enveloping boundary layer of the medium to be measured.

7. An optical detection apparatus according to claim 1 wherein said optical collecting means is arranged relative to said acoustically attenuating element such that said acoustically attenuating element is not significantly affected by a test light beam emitted by said light source.

8. An optical detection apparatus according to claim 7 wherein the test light beam is conveyed through a conical light pipe into said photoacoustic gas detector means such that a highly divergent light beam is formed that does not significantly irradiate said acoustically attenuating element positioned facing an opening in said conical light pipe.

9. An optical detection apparatus according to claim 8 wherein said photoacoustic gas detector means comprises a concave mirror for reflecting the test light beam passing out of the light pipe opening back to said conical light pipe.

10. An optical detection apparatus according to claim 1 wherein a passage extends between said photoacoustic gas detector means and the gas exchange means.

11. An optical detection apparatus according to claim 1 wherein said gas collecting point is connected to a gas producing means.

12. An optical detection apparatus according to claim 11 wherein said gas producing means is a chemical reactor.

13. An optical detection apparatus according to claim 12 wherein said chemical reactor is positioned at said gas collecting point.

14. An optical detection apparatus according to claim 13 wherein said chemical reactor comprises a reactor chamber containing a biologically active medium.

15. An optical detection apparatus according to claim 14 wherein said biologically active medium is immobilized on a support.

16. An optical detection apparatus according to claim 14 wherein said acoustically attenuating element separates said gas collecting point from a gas chamber of said photoacoustic gas detector means and supports said biologically active medium.

17. An optical detection apparatus according to claim 1 wherein said light source is thermal and is coupled to thermally modulated means for varying intensity by a phase lag of a periodic electric signal.

18. An optical detection apparatus according to claim 17 wherein the phase lag is carried out with a frequency of an integral frequency divider.

19. An optical detection apparatus according to claim 17 wherein the phase lag is carried out with an integral partial frequency of an alternating electric power source.

20. An optical detection apparatus according to claim 19 wherein the modulated intensity of said source is checked by a phase lag length.

21. An optical detection apparatus according to claim 20 wherein an additional light detector checks the modulated intensity of said source by measuring the phase lag length.

22. An optical detection apparatus according to claim 1 wherein said signal processing means comprises a selective amplifier and a signal analysis means, said signal analysis means subdividing a period of useful signals supplied by a microphone into at least two time slots and signal averaging in at least one of said time slots.

23. An optical detection apparatus according to claim 22 wherein said signal analysis means comprises a cyclic switch for subdividing the period of useful signals into time slots and a resistance element and capacitance elements for signal averaging.

24. An optical detection apparatus according to claim 23 wherein said cyclic switch is connected to at least two resistance capacitance elements, so that the phase between a modulating signal at said source and a signal at said microphone can be measured.

25. An optical detection apparatus according to claim 1 wherein said light source emits a test light beam producing photoacoustic signals; said optical collecting means comprises a semi-ellipsoidal concave mirror having an inner focal point provided with an optically partially transparent thermal source forming said light source, as well as a plane mirror-like counter-reflector having a central light exit opening positioned at a centrally bisecting plane of said semi-ellipsoidal mirror.

26. An optical detection apparatus for selectively detecting gases including vapors, comprising:
a thermal light source located within optical collecting means defining an optical path, said light source being coupled to thermally modulated means for varying intensity by a phase lag of a periodic electric signal;
a gas collecting cell in said optical path, said gas collecting gas including photoacoustic gas detector means for generating signals representative of gases detected in said gas collecting cell;
a monochromator in said optical path between said light source and said gas collecting cell;
gas exchange means for supplying gas to and discharging gases from said gas collecting cell, said gas exchange means including alternately closable valves; and
signal processing means, coupled to said detector means, for analyzing signals of said detector means.

27. An optical detection apparatus according to claim 26 wherein the phase lag is carried out with a frequency of an integral frequency divider.

28. An optical detection apparatus according to claim 26 wherein the phase lag is carried out with an integral partial frequency of an alternating electric power source.

29. An optical detection apparatus according to claim 28 wherein the modulated intensity of said source is checked by a phase lag length.

30. An optical detection apparatus according to claim 29 wherein an additional light detector checks the modulated intensity of said source by measuring the phase lag length.

31. An optical detection apparatus for selectively detecting gases including vapors, comprising:

a light source located within optical collecting means defining an optical path;
a gas collecting cell in said optical path, said collecting cell including photoacoustic gas detector means for generating signals representative of gases detected in said gas collecting cell;
a monochromator in said optical path between said light source and said gas collecting cell;
gas exchange means for supplying gases to and discharging gases from said gas collecting cell, said gas exchange means including alternately closable valves; and
signal processing means coupled to said detector means, for analyzing signals of said detector means, said signal processing means including a selective amplifier and a signal analysis means, said signal analysis means subdividing a period of useful signals supplied by a microphone into at least two time slots and signal averaging in at least one of said time slots.

32. An optical detection apparatus according to claim 31 wherein said signal analysis means comprises a cyclic switch for subdividing the period of useful signals into time slots and a resistance element and capacitance elements for signal averaging.

33. An optical detection apparatus according to claim 32 wherein said cyclic switch is connected to at least two resistance capacitance elements, so that the phase between a modulating signal at said source and a signal at said microphone can be measured.

34. A method of selectively detecting gases, including vapors, comprising the steps of:
emitting light from a light source located within an optical collecting means into a gas collecting cell in an optical path of the light source;
generating signals representative of gases detected in the gas collecting cell by photoacoustic gas detector means;
opening the photoacoustic gas detector means to surrounding gases through an acoustically attenuating element which is continuously permeable to gases so that the surrounding gases penetrate the photoacoustic gas detector means; and
analyzing signals generated by the photoacoustic gas detector means with signal processing means coupled to the photoacoustic gas detector means.

35. A method according to claim 34 wherein the gases to be measured are contained in a material having a boundary layer permeable to gases, the gases to be measured pass at least partially between the material and the photoacoustic gas detector means through a gas passage of the photoacoustic gas detector means and the gas permeable boundary layer.

36. A method according to claim 34 wherein the gases to be measured are dissolved in a liquid and are collected at a gas collecting point supplied with a liquid medium containing at least one dissolved gas.

37. A method according to claim 34 wherein a fluid medium is fed into and biologically reacted in a reactor containing at least one substrate such that dissolved gases are formed.

38. A method according to claim 34 wherein a medium is fed into a reactor containing dissolved substances which are biologically reacted in a reactor to form gases in dissolved form and to contain the dissolved substances in the medium; an additive is supplied to reversibly or irreversibly block the biological reaction.

39. A method according to claim 34 wherein several suspended biologically active substances are supplied to a reaction chamber to react substrates supplied in a sequence of steps up to at least one gaseous product.

40. A method according to claim 34 wherein a plant organism, photosynthesized under action of light radiation is measured; and at least partial direct gas exchange is conducted between the plant organism and the photoacoustic gas detector means through a gas passage.

41. A method according to claim 34 wherein at least one of $CO_2$ and $CO$ are measured.

42. A method according to claim 41 wherein a phase position between signals at a light radiator and a microphone control the light source, the optical collecting means, the microphone and acoustic decoupling devices.

43. A method according to claim 34 wherein gas permeability and acoustic resistance of an acoustic decoupling device are measured.

* * * * *